United States Patent [19]

Washburn et al.

[11] Patent Number: 5,994,337
[45] Date of Patent: *Nov. 30, 1999

[54] EFFECTS OF 17α-DIHYDROEQUILENIN ON PLASMA LIPID AND LIPOPROTEIN, GLUCOSE, INSULIN CONCENTRATIONS, CORONARY ARTERY VASOMOTOR FUNCTION, AND REPRODUCTIVE ORGAN AND MAMMARY GLAND PROLIFERATION IN ATHEROSCLEROTIC MAMMALS

[75] Inventors: Scott A. Washburn, Winston-Salem; Thomas B. Clarkson, Clemmons; Michael R. Adams, Clemmons; Thomas C. Register, Clemmons; J. Koudy Williams, Clemmons; Janice D. Wagner, Kernersville; J. Mark Cline, Winston-Salem, all of N.C.; Steven J. Adelman, Hatfield, Pa.

[73] Assignees: Wake Forest University, Winston-Salem, N.C.; American Home Products Corporation, Madison, N.J.

[21] Appl. No.: 09/006,000

[22] Filed: Jan. 12, 1998

Related U.S. Application Data

[60] Provisional application No. 60/034,495, Jan. 13, 1997.
[51] Int. Cl.$^6$ ..................... A61K 31/56
[52] U.S. Cl. ........................ 514/182
[58] Field of Search .................. 514/182

[56] References Cited

U.S. PATENT DOCUMENTS

| | | | |
|---|---|---|---|
| 3,507,889 | 4/1970 | Marshall | 260/397.5 |
| 4,154,820 | 5/1979 | Simoons | 424/175 |
| 5,545,635 | 8/1996 | Bryant et al. | 514/177 |
| 5,719,137 | 2/1998 | Washburn et al. | 514/182 |

OTHER PUBLICATIONS

Washburn, S.A. et al., A Conjugated Equine Estrogen With Differential Effectsd on Uterine Weight and Plasma Cholesterol In the Rat. Am J Obstet Gynecol 1993; 169:251–6.

Wagner, J.D., et al., A Non–Feminizing Conjugated Equine Estrogen Decreases Artenal LDL Degradation and Improves Vascular Reactivity In Male Rhesus Monkeys (abstract). Circulation 1995; 92:1–627.

Merck Index; 10$^{th}$ Edition; (1983); p. 3159, #3154.

Cefalu, W.T. et al., The Effects of Hormone Replacement Therapy on Insulin Sensitivity in Surgically Postmenopausal Cynomolgus Monkeys (*Macaca fascicularis*). Am J Obstet Gynecol 1994;171:440–5.

Wagner, J.D. et al., Estrogen and Progesterone Replacement Therapy Reduces Lipoprotein Accumulation in the coronary Arteries of Surgically Postmenopausal cynomolgus macaques. J Clin Invest 1991;88–1995–2002.

Goodman A.L. et al., Composite Pattern of Circulating LH, FSH, estradiol, and Progsterone During the Menstrual Cycle in Cynomolgus Monkeys. Pro Soc Exp Biol Med 1977;155:479–81.

Wilson M.E. et al, Effects of a Natural Versus Artificial Environment on the Tempo of Maturation in in Female Rhesus Monkeys. Endocrinology 1988; 123:2653–61.

Williams J.K. et al., Effects of Hormone Replacement Therapy on Reactivity of Atherosclerotic Coronary Arteries in Cynomolgus Monkeys. J Am Coll Cardio 1994;24:1757–61.

Cline J.M. et al., Effects of Hormone Replacement Therapy on the Mammary gland of Surgically Postmenopausal Cynomolgus Macaues. Am J Obstet Gynecol 1996;174:93–100.

Cline J.M. et al., Divergent Effects of Hormone Replacement in Mammary and Endometrial Tissues of Macaques labstratct. Menopause 1995;2:255.

Cattoretti G. et al., Monoclonal Antibodies Against Recombinant Parts of the Ki–67 Antigen (MIB1 and MIB3) Detect Proliferating Cells in Microwave–Processed Formalin–Fixed Paraffin Sections. J Pathol 1992;168:357–63.

Lindholm J. et al., A Morphometric Filter Improves the Diagnostic Value of Morphometric Analyses of Frozen Histopathologic Sections from Mammary Tumors. Anal Cell Pathol 1992;4:443–9.

Williams J.K. et al., Determinants of Coronary Artery Reactivity in Premenopausal Female Cynomolgus Monkeys with Diet–Induced Atherosclerosis. Circulation 1994;90:983–7.

Hamm T.E. et al., Effects of Gender and Social Behavior on the Development of Coronary Artery Atherosclerosis in Cynomolgus Monkeys. Atherosclerosis 1983;221:48–57.

Collins P. et al., 17—Estradiol Attenuates Acetylcholine–Induced Coronary Arterial Constriction in Women but Not Men with Coronary Heart Disease. Circulation 1995;92:24–30.

Reis S.E. et al., Estrogen has an Acute Beneficial Effect on Coronary Vasoreactivity in Man [abstract]. Circulation 1995;92:1–249.

(List continued on next page.)

*Primary Examiner*—Raymond Henley, III
*Attorney, Agent, or Firm*—Pat Winston Kennedy, Esq.; Kilpatrick Stockton LLP

[57] ABSTRACT

The present invention relates to a method of using 17α-dihydroequilenin and metabolic conjugates thereof to prevent and reduce atherogenesis in males and females without causing endometrial proliferation in females and without producing feminizing changes in males. 17α-dihydroequilenin was evaluated for its effects on plasma lipid and lipoprotein, glucose, insulin concentrations, coronary artery vasomotor function, and reproductive organ and mammary gland proliferation in atherosclerotic mammals. 17α-dihydroequilenin was found to prevent endothelium-dependent vasoconstriction in males (p<0.05) and ovariectomized females (p<0.08). 17α-dihydroequilenin treatment increased plasma apolipoprotein A-1 concentrations (p<0.05) and lowered fasting insulin concentrations (p<0.05) without changing fasting plasma glucose concentrations in males. 17α-dihydroequilenin had no other effects on plasma lipid and lipoprotein concentrations in either males or females. Also, 17α-dihydroequilenin exhibited no trophic effects on the uterus, endometrium, or breast, and no effect on either prostatic or testicular weight. Thus, 17α-dihydroequilenin may prevent breast and prostatic hyperplasia and neoplasia, and has no feminizing effects on the male urogenital system or mammary gland.

4 Claims, 4 Drawing Sheets

OTHER PUBLICATIONS

Subbiah M.T.R. et al., Antioxidant Potential of Specific Estrogens on Lipid Peroxidation. J Clin Endocrinol Metab 1993;77:1095–7.

Wilcox J.G. et al., The Biological Effects of Individual Estrogen Components in Conjugated Equine Estrogens (CEE) and Their Possible Modulation of Insulin Resistance and Oxidation of LDL [abstract]. J Soc Gynecol Invest 1995;2:153.

Lyman G.W. et al., Assay for Conjugated Estrogens in Tables U sing Fused–Silica Capillary Gas Chromatography. J Chromatogr 1982;234:234–9.

Stern M. Pharmacology of Conjugated Oestrogens; Maturitas 1982;4:33–9.

Bhavnani, B., The Saga of the Ring B Unsaturated Equine Estrogens; *Endocrine Reviews,* 1988.

Bhavnani, B., Interaction of Ring B Unsaturated Estrogens with Estrogen Receptors of Human Endometrium and Rat Uterus, *Steroids,* 1991, vol. 56, Apr. pp. 201–210.

Dodge, J.A., Premarin Components: Uterine,Cholesterol Lowering, and Bone Metabolic Effects, Jun. 1996 Endocrine Research, Lilly Research Laboratories.

Stern, M., Pharmacology of Conjugated Oestrogens; *Elsener Bio–Medical Press,* 1982 pp. 332–339.

Bhavnani, B., et al., The Metabolism of Equilin in Normal Men; *J. Steriod Bio–chem,* vol. 17, pp. 217–223, 1982.

Washburn, S. et al., Effects of 17α–Dihydroequilenin on Rat Hippocampal Dendritic Spine Density; (1990).

Washburn, S. et al., 17α–Dihydroequilenin Increases Hippocampal Dendritic Spine Density of Ovariectomized Rats (1988).

Pharmacokinetics of 17β–Dihydroequilin Sulfate and 17β–Dihydroequilin in Normal Postmenopausal Women; *Journal of Clinical Endorcrinology and Metabolism,* vol. 78 No. 1, pp. 197–204, 1994.

Pharmacokinetics of Equilin and Equilin Sulfate in Normal Postmenopausal Women and Men; J. of Clinical Endo. and Meta., 1983, vol. 56, No. 5, pp. 1048–1056.

Effect of 17α–dihydroequilin sulfate, a water–soluble estrogen of PremarinR, on atherosclerosis in cholesterol–fed rabbits, Tuesday, Oct. 11, 1994:Poster Abstracts, p. 102, #40.

Physicians' Desk Reference; p. 2787 1996.

Washburn, S.A., et al., 17α–Dihydroequilenin increases hippocampal dendritic spine density of ovariectomized rats, Brian Research, Accepted Feb. 25, 1997; pp. 241–244.

EFFECTS OF 17α-DIHYDROEQUILENIN ON PLASMA LIPID AND LIPOPROTEIN, GLUCOSE, INSULIN CONCENTRATIONS, CORONARY ARTERY VASOMOTOR FUNCTION, AND REPRODUCTIVE ORGAN AND MAMMARY GLAND PROLIFERATION IN ATHEROSCLEROTIC MAMMALS

BACKGROUND OF THE INVENTION

This application claims the benefit of U.S. Provisional Application No. 60/034,495 filed Jan. 13, 1997.

The present invention relates to a method of using 17α-dihydroequilenin and metabolic conjugates thereof to reduce and prevent ischemic heart disease in males and females without causing endometrial proliferation in females and without producing feminizing changes in males. More particularly, the present invention relates to the use of 17α-dihydroequilenin in atherosclerotic mammals and to evaluate its effects on plasma apolipoprotein, glucose, insulin concentrations, coronary artery vasomotor function, and reproductive organ and mammary gland proliferation.

Postmenopausal estrogen replacement therapy has gained wide recognition as a lifelong preventive regimen for the reduction of osteoporotic fracture and ischemic heart disease. Unfortunately, good scientific evidence has failed to persuade the majority of menopausal women that the benefits of long-term estrogen replacement therapy are worth the inconvenience or anxiety resulting from its side effects, especially vaginal bleeding and the putative increase in breast cancer risk. Additionally, most of the evidence of estrogen effects in preventing ischemic heart disease in the United States is from studies that used unopposed conjugated equine estrogens. The current evidence is unclear as to whether the addition of progestins, necessary to prevent iatrogenically induced endometrial carcinoma, may either partially or completely negate the cardioprotective effect of unopposed estrogens. Several of the inventors have described a component of Premarin® (Wyeth-Ayerst, Princeton, N.J.), 17α(-dihydroequilenin (DHEN), that caused no uterine hypertrophy in ovariectomized rats compared with ovariectomized controls and compared with a doubling of uterine weight in Premarin treated ovariectomized rats. [Washburn S A et al., A conjugated equine estrogen with differential effects on uterine weight and plasma cholesterol in the rat. *Am J Obstet Gynecol* 1993;169:251–6]. It was determined that DHEN caused a 70% reduction in total plasma cholesterol concentrations compared with ovariectomized controls and compared with a 15% reduction of total plasma cholesterol in ovariectomized rats treated with oral Premarin®.

Currently, there are no hormone replacement therapies that deliver established benefits to menopausal females and males such as the prevention and/or reduction of atherosclerotic heart disease without causing endometrial proliferation or other side effects of the type previously mentioned. Thus, there remains a need for an alternative hormone replacement therapy for menopausal women and men without side effects or the need to take concomitant progestin therapy.

SUMMARY OF THE INVENTION

The present invention is directed to a method of using 17α-dihydroequilenin (DHEN), a constituent of conjugated equine estrogens, to reduce and prevent atherogenesis by 1) preventing endothelium-dependent vasoconstriction in both males and menopausal females; 2) increasing apolipoprotein A-l; 3) improving insulin sensitivity (while decreasing plasma insulin concentrations without reducing glucose concentrations); 4) reducing LDL accumulation; and 5) reducing arterial peroxidation. Further, DHEN does not appear to have any proliferation or trophic effects on the female macaque reproductive or mammary organs, thus, making DHEN an attractive single-agent hormone replacement therapy that may be used without the need for a concomitant progestin. Additionally, DHEN does not appear to have any feminizing effects on the male genitourinary system or mammary gland, making DHEN a potential treatment for men in the prevention of ischemic heart disease without the feminizing side effects of the traditional estrogen regimen and may prevent prostate hyperplasia and neoplasia.

The present invention further provides a method of using DHEN for the treatment of the above conditions and/or diseases by administering a therapeutically effective amount of DHEN or a mammalian metabolic conjugate thereof and an appropriate pharmaceutical carrier.

In preventing and/or reducing atherosclerosis, DHEN or a metabolic conjugate thereof is administered in therapeutically effective amounts to mammals with atherosclerosis or to those susceptible to atherosclerosis or conditions related thereto. Other groups of mammals that are susceptible to the risk of atherosclerosis will be apparent to those skilled in the art.

The term "therapeutically effective amount" as used in the present invention is defined as the dose which provides effective treatment or prevention of the above described conditions and/or diseases to mammals, in particular humans.

The mammalian metabolic conjugates used in the present invention are sulfates and glucuronides of 17α-dihydroequilenin. 17α-dihydroequilenin can be used either in the form of a mono- or di-conjugate. It is further contemplated that any derivative of 17α-dihydroequilenin that forms 17α-dihydroequilenin or conjugate thereof in vivo may be used in treating or preventing the conditions and/or diseases described hereinabove.

In another aspect of the present invention, mammals susceptible to atherosclerotic heart disease include men and women.

In yet another aspect of the present invention, the mammal susceptible to atherosclerotic heart disease is a menopausal woman.

The route of administration for DHEN is selected from the group consisting of oral, intravenous, parental, transdermal, rectal, intravaginal, intranasal, and intrabronchial administration. However, oral dosing is the preferred route of administration.

The preceding and further objects of the present invention will be appreciated by those of ordinary skill in the art from a reading of the detailed description of the preferred embodiments which follow, such description being merely illustrative of the present invention.

BRIEF DESCRIPTION OF THE DRAWINGS

Some of the features and advantages have been stated, other will become apparent from the detailed description which follows, and from the accompanying drawings, in which.

DESCRIPTION OF THE PREFERRED EMBODIMENTS

Figure 3:
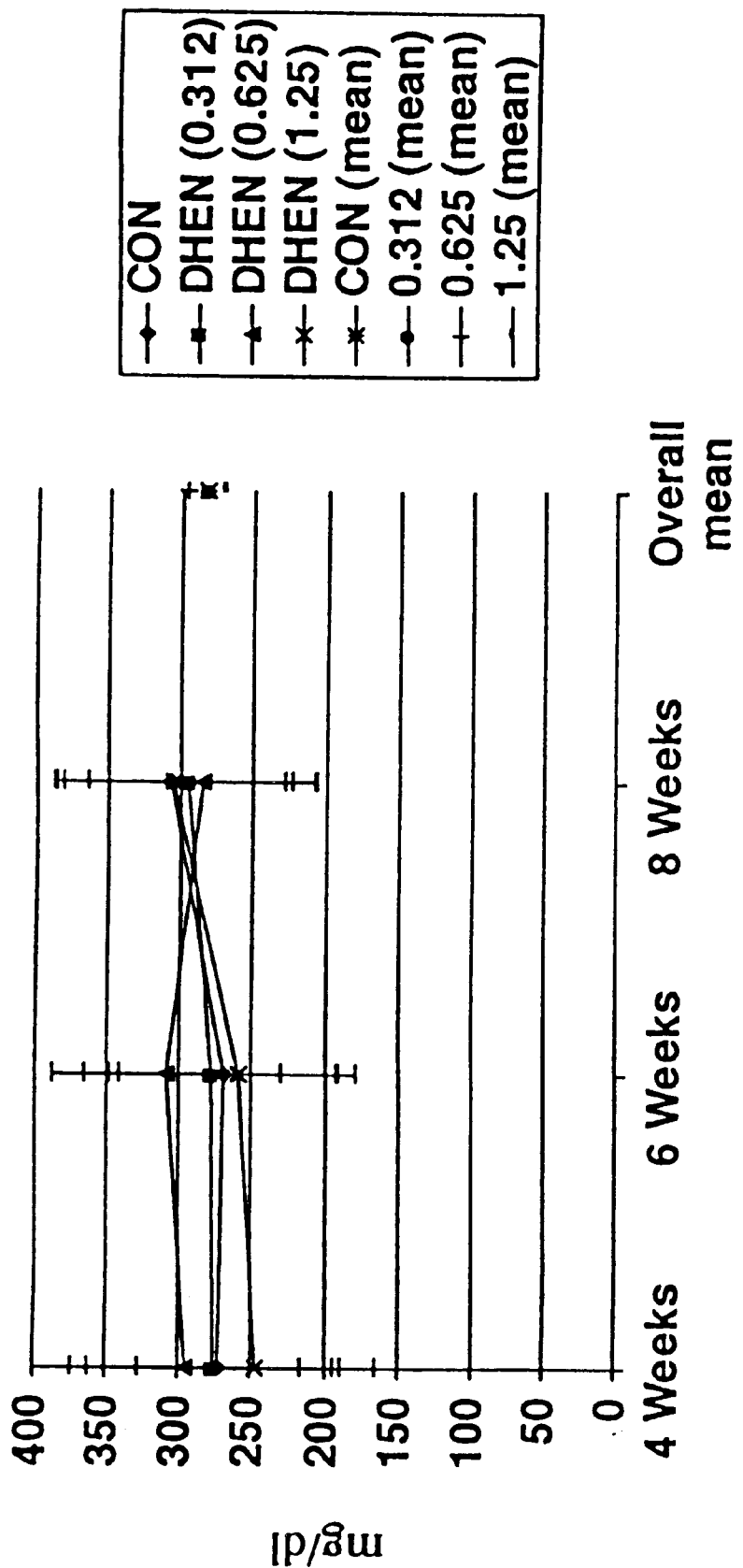
FIG. 3 represents the total plasma cholesterol in female rhesus monkeys. OVX, ovariectomized; CON, control.
Figure 4:
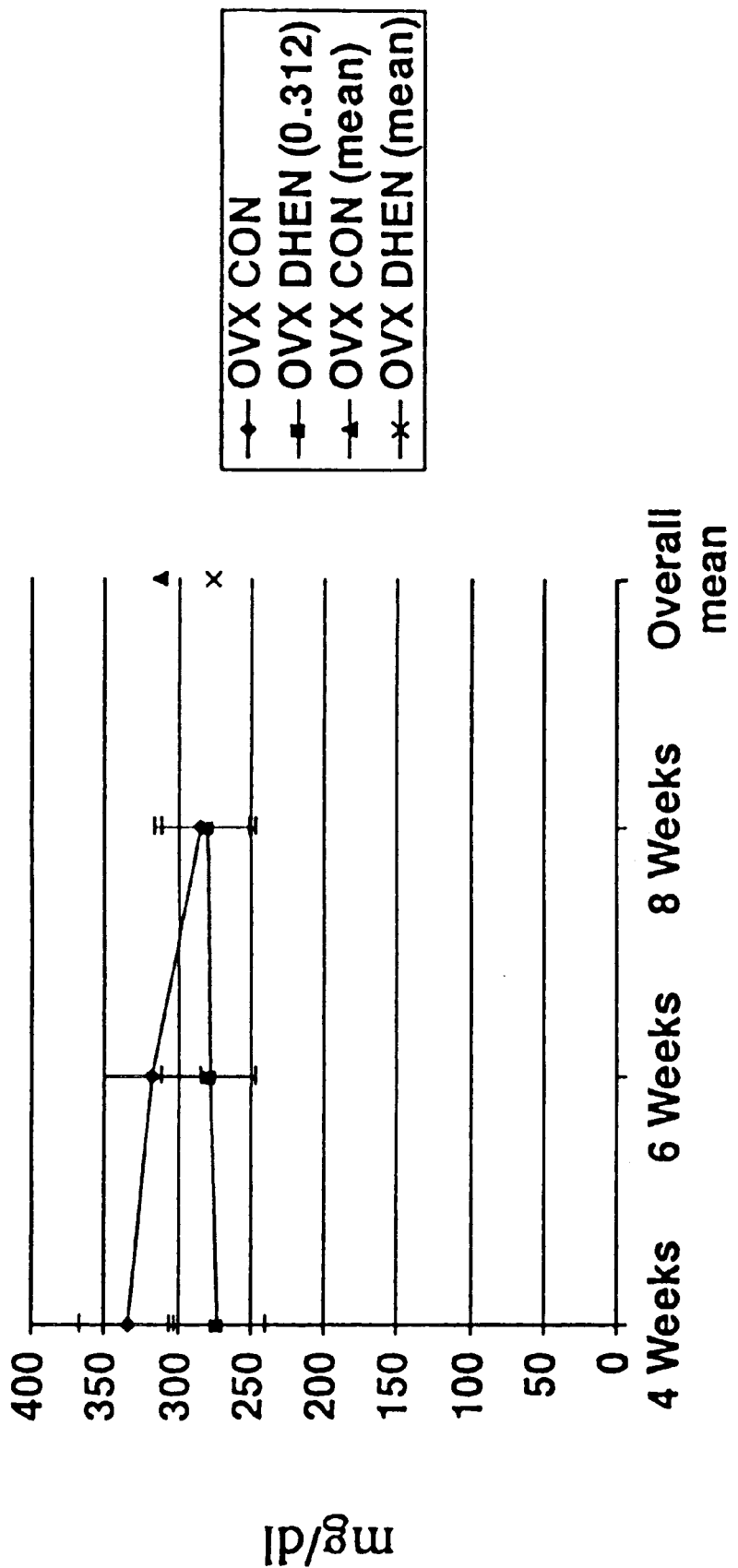
FIG. 4 represents total plasma cholesterol in male rhesus monkeys. CON, control.

In accordance with the present invention, atherosclerotic male and female rhesus monkeys were evaluated to assess the effect of DHEN on plasma lipid and lipoprotein concentrations, fasting plasma glucose and insulin concentrations, coronary artery vasomotion, endometrial proliferation in the females and prostatic and testicular weight changes in the males. Doses of approximately 0.3 mg/kg/day for females and approximately 1.25 mg/kg/day in the males were mixed into the moderately atherogenic diet. These doses were based on the results of an 8-week dose-finding study in a separate group of rhesus monkeys to determine an appropriate dose of DHEN that would favorably affect plasma lipid and lipoprotein concentrations as shown in FIGS. 3 and 4.

50 adult female and 33 adult male rhesus macaques were randomized to treatment by lifetime dietary cholesterol exposure and ratio of total plasma cholesterol to high-density lipoprotein cholesterol. The female treatment groups were intact female controls (n=9), ovariectomized controls (n=16), ovariectomized plus 0.3 mg/kg/day 1 7-dihydroequilenin (n=17) and ovariectomized plus subcutaneous estradiol (n=7). The male treatment groups were control (n=16) and 1.25 mg/kg/day 17α-dihydroequilenin (n=17). Treatment lasted 5 weeks. Longitudinal assessments of plasma lipid and lipoprotein and glucose and insulin concentrations were performed. Coronary artery vasomotor function was assessed by quantitative coronary angiography 1 week after initiation of treatment. Morphologic and immunohistochemical assessments of proliferation index values of reproductive organs and mammary glands were done at necropsy.

Based on the studies conducted, 17α-dihydroequilenin prevented endothelium-dependent vasoconstriction in males ($p<0.05$) and ovariectomized females ($p<0.08$). 17α-dihydroequilenin treatment increased plasma apolipoprotein A-l concentrations ($p<0.05$) and lowered fasting insulin concentrations ($p<0.05$) without changing fasting plasma glucose concentrations in males. 17α-dihydroequilenin had no other effects on plasma lipid and lipoprotein concentrations in either males or females. 17α-dihydroequilenin exhibited no trophic effects on the uterus, endometrium, or breast. Further, no effect on either prostatic or testicular weight was observed.

Based on the results of the present invention, 17α-dihydroequilenin appears to represent a single-agent hormone therapy for reduction of ischemic heart disease risk for both menopausal women and men. It has no apparent trophic effects on reproductive organs or mammary glands of female and male rhesus macaques.

1. Material and methods

Figure 1:
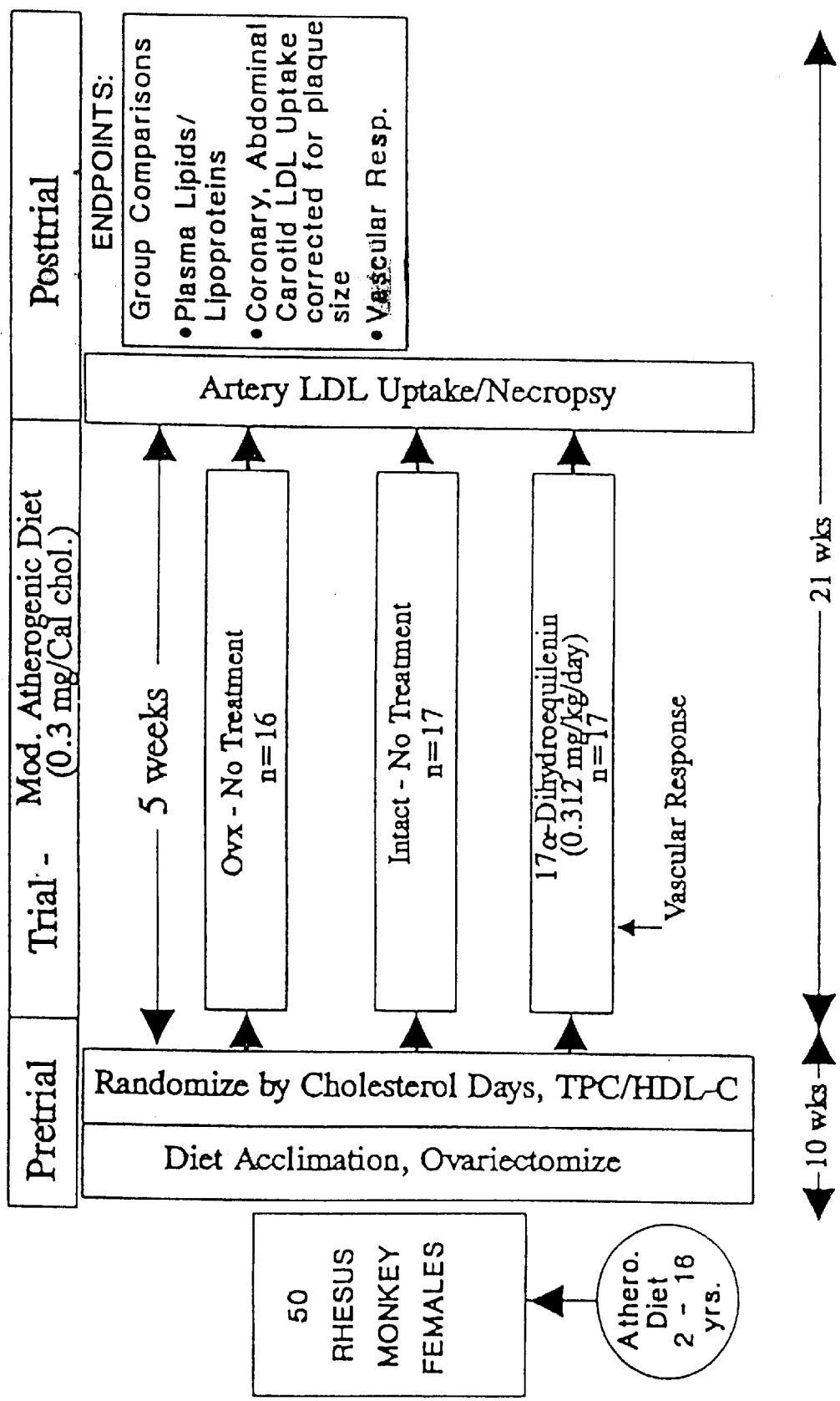
FIG. 1 represents a time-line of the experiments for female monkeys (n=50)
Figure 2:
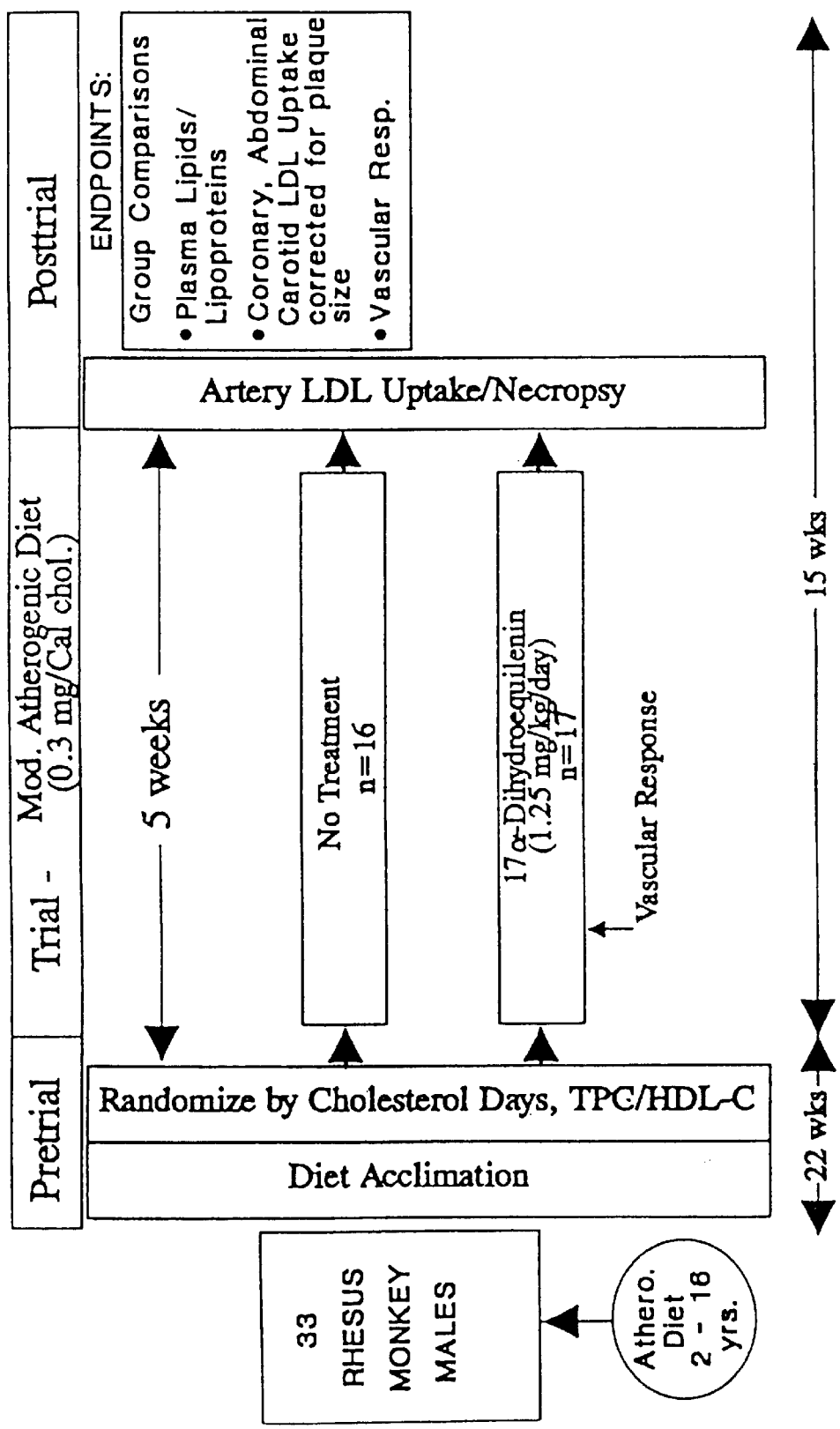
FIG. 2 represents a time-line of the experiments for male monkeys (n=33).

Studies conducted represent a randomized, placebo-controlled trial of 50 atherosclerotic female and 33 atherosclerotic male rhesus macaques that were part of a breeding colony at the Comparative Medicine Clinical Research Center of the Bowman Gray School of Medicine. The animals had consumed a moderately atherogenic diet for an average of 10 years, and complete records were kept regarding their dietary, experimental, and reproductive histories as members of the breeding colony. The experimental design is depicted in FIGS. 1 and 2.

Animals were randomized to treatment group by cholesterol days (amount of dietary cholesterol consumed during the animals' lifetime) and by the fasting total plasma cholesterol/high-density lipoprotein cholesterol (HDL) ratio obtained after acclimatization to the control diet.

Males received about 1.25 mg/kg/day DHEN mixed into a moderately atherogenic diet (0.3 mg/cal cholesterol) or the diet alone (controls). The females were randomized to three groups: 1) intact control, 2) ovariectomized control, or 3) ovariectomized plus about 0.3 mg/kg/day DHEN. All females were fed the same moderately atherogenic diet as the males. Approximately half way through the experiment a fourth treatment group of female monkeys (n=7) was started because of their concern that experimental stress (single-cage housing, multiple phlebotomies, angiography, and arterial and venous catheter placements) might decrease plasma estradiol concentrations and, thus, prevent the (intact control) group from serving as "positive" controls. The animals in the fourth group were similar in age, cholesterol days, and total plasma cholesterol/HDL ratio to the other females. The animals in this fourth group were ovariectomized, and subcutaneous implants containing 17β-estradiol were placed 2 weeks after ovariectomy to coincide with initiation of treatment in the DHEN groups (1 week before angiography). Treatment was for 5 weeks to avoid any changes in plaque size that might confound low-density lipoprotein (LDL) metabolism studies [see Wagner J D et al., A non-feminizing conjugated equine estrogen decreases artenal LDL degradation and improves vascular reactivity in male rhesus monkeys [abstract]. *Circulation* 1995;92:1–6273.

All procedures and treatments were approved by the Bowman Gray School of Medicine Animal Care and Use Committee and complied with applicable state and federal animal care guidelines.

Baseline samples were obtained 2 weeks after ovariectomy to measure fasting total plasma cholesterol and plasma HDL, triglyceride, glucose, and insulin concentrations. Two weeks after ovariectomy, treatment was begun. The estradiol group was anesthetized and underwent a brief procedure for placement of two subcutaneous estradiol implants. After 1 week of treatment, quantitative angiography was performed with intracoronary acetylcholine and nitroglycerin infusions. Plasma samples were taken to measure concentrations of 17β-estradiol, testosterone, androstenedione, dihydroepiandrosterone sulfate (DHEAS), and DHEN.

Two weeks after angiography plasma concentrations of total cholesterol, HDL, triglycerides, apolipoproteins A-l, B, and E, and fasting glucose and insulin were determined. Plasma concentrations of estradiol, androstenedione, DHEAS, testosterone, and DHEN were also determined. The animals underwent LDL metabolism studies after the fifth week of treatment and then necropsy. Standard measures of plaque extent in the coronary and iliac arteries, thoracic and abdominal aortas, common carotid artery and carotid bifurcation, and basilar arteries were determined [Wagner J D et al., Estrogen and progesterone replacement therapy reduces lipoprotein accumulation in the coronary arteries of surgically postmenopausal cynomolgus macaques. *J Clin Invest* 1991;88:1995–2002]. Mammary and reproductive tissues were collected from all animals as described below.

2. Analytic methods

Plasma lipids and lipoproteins. Plasma concentrations of total plasma cholesterol, HDL, triglycerides, and glucose were determined with a COBAS-FARA (Roche, Nutley, N.J.) autoanalyzer. LDL plus very-low-density lipoprotein cholesterol concentrations were determined by subtracting HDL concentrations from total plasma cholesterol concentrations. Total plasma cholesterol, HDL, triglycerides, and LDL concentrations were determined at baseline, at 1 and 3 weeks after starting treatment, and at necropsy (5 weeks after starting treatment). Plasma insulin concentrations were determined with a standard radioimmunoassay that has been described in [Cefalu W T et al., The effects of hormone replacement therapy on insulin sensitivity in surgically postmenopausal cynomolgus monkeys (*Macaca fascicularis*). *Am J Obstet Gynecol* 1994;171:440–5].

Plasma aliquots for apolipoprotein quantitation were stored at −70° C., and apolipoproteins were quantitated by enzyme-linked immunosorbent assay (ELISA). The ELISA for apolipoprotein A-l used previously published methods, and a similar protocol was used for assaying apolipoproteins B100 and E. The ELISA for apolipoproteins A-l, B, and E quantification is a 4-day noncompetitive sandwich assay that uses monospecific immunopurified antibodies raised in goats. The secondary antibody is crosslinked to horseradish peroxidase. Color produced in the presence of the chromogen o-dianisidine and hydrogen peroxide is proportional to the apolipoprotein concentration in each sample. The secondary standard and plasma controls that were run in duplicate on each microtiter plate were pooled plasma samples from cynomolgus monkeys. Secondary standards were standardized against a primary standard of purified apolipoprotein A-l, LDL-apolipoprotein B100. For apoprotein quantification unknown plasma samples were diluted over the range of 1:125,000 to 1:1,000,000 for apolipoprotein A-l and 1:1250 to 1:10,000 for a polipoprotein B. A minimum of three different dilutions of each unknown were assayed to check for nonparallelity of response between unknowns and standards [see Wagner J D et al., Estrogen and progesterone replacement therapy reduces lipoprotein accumulation in the coronary arteries of surgically postmenopausal cynomolgus macaques. *J Clin Invest* 1991;88:1995–2002].

Sex hormones. Plasma concentrations of androstenedione, estradiol, DHEAS, and testosterone were determined by ELISA (Diagnostic Products Corporation, Los Angeles) at the Endocrine Assay Laboratory of the Yerkes Regional Primate Center, Atlanta, by using methods in accordance with Goodman A L et al., Composite pattern of circulating LH, FSH, estradiol, and progesterone during the menstrual cycle in cynomolgus monkeys. *Proc Soc Exp Biol Med* 1977;155:479–81 and Wilson M E et al, Effects of a natural versus artificial environment on the tempo of maturation in female rhesus monkeys. *Endocrinology* 1988; 123:2653–61].

Quantitative coronary angiography. Responses of proximal epicardial sections of the left circumflex coronary artery to dilute ($10^{-6}$ mol/L) acetylcholine (endothelium-dependent dilation) and ($10^{-6}$ mol/L) nitroglycerin (endothelium-independent dilation) was measured by quantitative coronary angiography [Williams J K et al., Effects of hormone replacement therapy on reactivity of atherosclerotic coronary arteries in cynomolgus monkeys. *J Am Coll Cardiol* 1994;24:1757–61]. Percent change (compared maximal lumen diameter at end-diastole during intracoronary infusion of 5% dextrose in water) was measured in the entire coronary artery section and separately in the proximal, middle, and distal segments of the coronary artery section. This was done to determine whether there was an effect of treatment on certain parts of the epicardial coronary artery.

Reproductive and mammary gland assessments.

TISSUE COLLECTION. Reproductive and mammary gland tissues were collected from all animals at the end of the study (uterus, vagina, and mammary glands from females; prostate, testicles, epididymis, and mammary glands from males). Uterine, ovarian, prostatic, and testicular weights were measured. Tissues were then fixed in 4% buffered paraformaldehyde for 24 hours and stored in 70% ethanol. Tissues were trimmed to 3 mm in thickness, embedded in paraffin, and sectioned at 5 um for immunostaining [see Cline J M et al., Effects of hormone replacement therapy on the mammary gland of surgically postmenopausal cynomolgus macaques. *Am J Obstet Gynecol* 1996;174:93–100].

HISTOPATHOLOGIC STUDY. Mammary gland slides were subjecuvely classified as atrophic, hyperplasia, or neither. The treatment group of each animal was obscured during the procedure to prevent observer bias. Hyperplasia, atypia, cystic lesions, and the presence of intraluminal protein or intraepithelial fat globules mimicking secretory activity were noted. Lesions were independently graded as none, mild, moderate, or severe [see Cline J M et al., *Am J Obstet Gynecol, supra*].

MORPHOMETRY AND STEREOLOGIC MEASUREMENTS. Measurements were made with a Macintosh (Apple, Cupertino, Calif.) computer-based video image analysis system (Power Macintosh [Apple] 7100, Hitachi [Hitachi, Lyndhurst, N.J.] VK-C370 video camera, Scion [Scion, Frederick, Md.] LG-3 frame-grabber, and public domain software [National Institutes of Health Image]) by use of methods disclosed in Cline J M et al., *Am J Obstet Gynecol*, supra and Cline J M et al., Divergent effects of hormone replacement in mammary and endometrial tissues of macaques labstract]. *Menopause* 1995;2:255].

Endometrial thickness was measured as greatest thickness perpendicular to the luminal surface, from histologic sections. Mammary gland thickness was measured similarly, perpendicular to the skin. Estimates of the relative proportions of tissue components in the endometrium-and mammary gland were made by tracing epithelium and luminal area in three randomly selected microscopic fields at a magnification of ×200 for the endometrium and ×40 for the mammary gland [Cline J M et al., *Am J Obstet Gynecol, supra*]

PROLIFERATION ASSESSMENTS. Staining procedures were done on fixed paraffin-embedded tissues. The basic staining procedure uses an avidin-biotin-peroxidase method modified for antigen retrieval from paraffin-embedded tissue. To assess proliferation, the Ki-67 MIB-I monoclonal antibody assay was used (Immunotech, Marseille, France) [see Cattoretti G et al., Monoclonal antibodies against recombinant parts of the Ki-67 antigen (MIB1 and MIB3) detect proliferating cells in microwave-processed formalin-fixed paraffin sections. *J Pathol* 1992;168:357–63].

QUANTIFICATION OF IMMUNOHISTOCHEMICAL STAINING. Immunostained cells were quantified by cell counting in sections by an observer blinded to treatments. In the uterus, epithelial and stromal cells in the basalis and functionalis were counted. Labeled cell nuclei were identified ac unlabeled (O), or weakly (+), moderately (++), or intensely (+++) labeled. At least 100 cells per slide were counted at three different sites for each combination of animal, tissue site, and stain type. Cells were counted with a grid-filtering technique to avoid bias in the selection of cells counted [see Lindholm J et al., A morphometric filter improves the diagnostic value of morphometric analyses of frozen histopathologic sections from mammary tumors. *Anal Cell Pathol* 1992;4:443–9].

3. Statistical methods. Plasma lipid, lipoprotein, and sex hormone values and arterial plaque extent were compared by group after baseline values were adjusted for, and they were analyzed by analysis of variance with the SAS statistical package (Research Triangle Park, N.C.). Analysis of variance was used to compare the vasomotor response of artery segments among groups. Data were adjusted before variance analysis to account for multiple segments from each monkey. Analyses of the morphometry and immunohistochemistry were performed with the Mann-Whitney U test with Bonferroni corrections for multiple comparisons, Kruskal-Wallis test, $\chi^2$ test, and Spearman's rank correlation test. For all other data reported, significance was assumed at the $p<0.05$ level. Data are reported as the mean±SD.

4. Results

Clinical events: Myocardial ischemia. There were five deaths during angiography, three in the ovariectomized control group and one each in the male control and male DHEN groups. A sixth monkey (ovariectomized DHEN group) was found dead the morning after angiography, but had fully recovered from the procedure and was clinically stable at least 6 hours after the angiography. The angiographic protocol was adjusted as a result of the three deaths in the ovariectomized control group. This included continuous electrocardiographic monitoring during angiography and decreasing the infusion of acetylcholine from the standard 2 minutes to the point of ischemia (defined as significant ST segment elevation). This change prevented lethal arrhythmias. In addition, it was noted that both males and females not treated with DHEN had intractable ischemia in spite of nitroglycerin infusions after the acetylcholine infusion, whereas in animals treated with DHEN changes resolved promptly during the 2-minute nitroglycerin infusion.

Plasma Lipid, lipoprotein, apolipoprotein, glucose, and insulin concentrations. There were no differences in total plasma cholesterol, HDL, and triglyceride concentrations with treatment or between groups in either the females or males. Apolipoproteins A, B, and E concentrations also were not different with treatment or between groups in the female monkeys. The males had similar concentrations of apolipoprotein B and, although not significant, apolipoprotein E concentrations tended to be lower in the DHEN-treated males ($p<0.08$, as shown below in Table I).

TABLE I

| | Apolipoprotein A, B, and E concentrations in male rhesus macaques* | | |
|---|---|---|---|
| Group | Apolipoprotein A-1 | Apoliprotein B | Apolipoprotein E |
| Control | 171.6 (18.3) | 159.6 (19.2) | 7.8 (1.1) |
| DHEN | 225.6 (18.9)† | 120.6 (19.9) | 5.2 (1.1) |

*Adjusted for baseline values.
†p < 0.05, compared with control group.

The males treated with DHEN did have a 31% increase in apolipoprotein A-1 concentrations compared with the control males ($p<0.05$, Table I). Fasting plasma glucose concentrations were not affected by any treatment in either the males or the females; however, the DHEN-treated males had a 43% reduction in fasting insulin concentration compared with male controls ($p<0.02$, shown below in Table II).

TABLE II

| Fasting plasma glucose and insulin concentrations of female and male rhesus macaques after 3 weeks of treatment. | | |
|---|---|---|
| Group | Glucose (mmol/L) | Insulin (pmol/L) |
| Females | | |
| Intact controls | 66.8 (3.6) | 59.0 (15.4) |
| Ovariectomized controls | 63.9 (3.2) | 63.0 (12.8) |
| Ovariectomized DHEN | 63.8 (3.1) | 58.8 (12.4) |
| Ovariectomized plus estradiol | 58.3 (4.3) | 43.8 (19.1) |
| Males | | |
| Control | 67.2 | 97.5 (12.4) |
| DHEN | 69.2 | 55.5 (12.0)* |

Amounts are mean ± SE.
p < 0.02, compared with male control group.

Sex steroids. Estradiol and DHEAS concentrations of the females were measured at 1 week of treatment, as were total testosterone and DHEAS concentrations of the males. Estradiol, testosterone, androstenedione, and DHEAS concentrations of all animals were measured after 4 weeks of treatment (see Table III below).

TABLE III

| | Plasma sex steroid concentrations (in picograms per milliliter) in female and male rhesus macaques | | | | | | |
|---|---|---|---|---|---|---|---|
| Group | $E_2$ (Week 1) | $E_2$ (Week 2) | T (Week 1) | T (Week 4) | DHEAS (Week 1) | DHEAS (Week 4) | $A_4$ (Week 4) |
| FEMALES | | | | | | | |
| Intact controls | 79.6 (12.0)* | 48.5 (15.2)† | — | 0.045 (.490) | 7.04 (2.92) | 5.14 (2.70) | 1.6. (0.40) |
| Ovariecto-mized controls | 12.4 (9.5) | 9.7 (13.4) | — | 0.021 (0.41) | 6.53 (2.31) | 6.34 (2.37) | 2.41 (0.35) |
| Ovariecto-mized DHEN | 61.6 (9.8)* | 46.6 (12.9)† | — | 0.03 (0.41) | 9.82 (2.38) | 11.02 (2.29) | 2.36 (0.34) |
| Ovariecto-mized | 123.3 (14.4)* | 74.8 (18.2)‡ | — | 0.00 (0.58) | 9.41 (3.49) | 7.06 (3.23) | 1.66 (0.48) |

TABLE III-continued

Plasma sex steroid concentrations (in picograms per milliliter) in female and male rhesus macaques

| Group | $E_2$ (Week 1) | $E_2$ (Week 2) | T (Week 1) | T (Week 4) | DHEAS (Week 1) | DHEAS (Week 4) | $A_4$ (Week 4) |
|---|---|---|---|---|---|---|---|
| estradiol | | | | | | | |
| MALES | — | 20.7 | 2.05 | 2.72 | 10.21 | 10.22 | 3.34 |
| Control | | (12.0) | (0.44) | (0.38) | (2.24) | (2.14) | (0.32) |
| DHEN | — | 125.8 | 1.99 | 1.54 | 12.92 | 10.43 | 2.62 |
| | | (12.9)§ | (1.54) | (0.40)\| | (2.38) | (2.21) | (0.33) |

Amounts are mean ± SE. $E_2$, Estradiol; T, testosterone; $A_4$, and andostenedione.
\*p < 0.001, compared with ovariectomized control group.
† p < 0.05, compared with ovariectomized control group.
‡ p < 0.01, compared with ovariectomized control group.
§ < 0.0001, compared with male control group.
\| p < 0.04, compared with male control group.

As expected, plasma estradiol concentrations were higher in both the intact control and ovariectomized estradiol groups compared with the ovariectomized control females. However, the 4-week estradiol concentrations were lower than those necessary to restore endothelium-independent vasodilation in female macaques in a previous study [see Williams J K et al., Determinants of coronary artery reactivity in premenopausal female cynomolgus monkeys with diet-induced atherosclerosis. *Circulation* 1994;90:983–7. Plasma concentrations of DHEN were 92.6±51.3 ng/ml in the females and 389.6±116.7 ng/ml in the males. The apparent increase in plasma estradiol concentrations in both the DHEN-treated females and males may reflect the 0.03% cross-reactivity of the estradiol ELISA for dihydroequilenin (Pittaway Del. Unpublished observations).

Coronary artery vasomotor function. Changes in coronary artery diameter in response to intracoronary infusion of acetylcholine ($10^{-6}$ mol/L) in whole arteries are shown in Table IV below. It should be noted that the number of animals in each group is different from the beginning of the experiment as a result of a roll of angiogram tape being lost. Responses for proximal, middle, and distal segments of each artery to both acetylcholine and nitroglycerin were compared, but there were no differences in the response of the individual segments compared with the entire artery.

Table IV. Percent change luminal diameter of the left circumflex coronary artery to $10^{-6}$ mol/L acetylcholine and nitroglycerin in male and female rhesus macaques.

TABLE IV

| Group | ACh (No.) | NTG (No.) | Change in baseline ACh* (%) | Change in baseline NTG* (%) |
|---|---|---|---|---|
| FEMALES Intact controls | 5 | 4 | 3.1 (4.0)† | 2.7 (2.5) |
| Ovariectomized controls | 9 | 8 | -4.1 (1.7) | 0.7 (0.6) |
| Ovariectomized DHEN | 11 | 10 | -1.3 (1.1)‡ | 2.9 (1.3) |
| Ovariectomized plus estradiol | 5 | 2 | -7.8 (3.6) | -5.2 (1.2) |

TABLE IV-continued

| Group | ACh (No.) | NTG (No.) | Change in baseline ACh* (%) | Change in baseline NTG* (%) |
|---|---|---|---|---|
| MALES Controls | 12 | 12 | -4.0 (1.2) | 1.5 (0.8) |
| DHEN | 11 | 6 | -0.9 (0.8)§ | 3.5 (1.2) |

Amounts are mean ± SEM. ACh, Acetylcholine; NTG, nitroglycerin.
\*Baseline is maximum diameter at end-diastole during 5% dextrose in water infusion.
†p < 0.05, compared with ovariectomized controls; p > 0.1, compared with ovariectomized DHEN group.
‡p < 0.08, compared with ovariectomized controls.
§p < 0.05, compared with male controls.

Amounts are mean ±SEM. ACh, Acetylcholine; NTG, nitroglycerin.

* Baseline is maximum diameter at end-diastole during 5% dextrose in water infusion.

† p<0.05, compared with ovariectomized controls; p>0.1, compared with ovariectomized DHEN group.

‡ p<0.08, compared with ovariectomized controls.

§ p<0.05, compared with male controls.

Atherosclerosis extent. There were no differences in the extent of coronary artery atherosclerosis between female treatment groups or between the two male treatment groups. The males had significantly larger atherosclerotic plaques than the females, which had been intact and cycling before this experiment (p<0.05). This is consistent with data we have reported previously regarding male and female differences in diet-induced atherosclerosis in nonhuman primates [see Hamm T E et al., Effects of gender and social behavior on the development of coronary artery atherosclerosis in cynomolgus monkeys. *Atherosclerosis* 1983;221:48–57].

Reproductive organ weights. DHEN treatment did not induce changes in uterine weight relative to ovariectomized controls (DHEN, 1.93±1.19 gm; controls, 2.29±1.15 gm). Mean uterine weight was greatest in intact controls (5.70±2.70 gm), but estradiol treatment of ovariectomized animals resulted in increased uterine weights (4.24±1.84 gm), which did not differ from that of cycling animals. Both the intact control and the ovariectomized estradiol groups had statistically greater uterine weights than either the ovariectomized control or the ovariectomized DHEN groups (p<0.05). Prostatic and testicular weights were not affected by DHEN treatment.

Histopathologic examination. Atrophy of the uterus, vagina, cervix, and mammary glands was seen in all ovariectomized control animals. Reproductive tract morphologic features in nonovariectomized females was variable and consistent with a cycling state. In all estradiol treated monkeys, there was endometrial hyperplasia and stromal edema. Estradiol also induced vaginal keratinization and squamous metaplasia of the endocervix in all animals in the group. Ovariectomized DHEN-treated monkeys were histologically indistinguishable from control females at all tissue sites. Mammary gland development in estradiol-treated females exceeded that seen in ovariectomized controls. Gynecomastia was not apparent in either the DHEN-treated male group or the ovariectomized estradiol group. No treatment-associated prostatic or testicular changes were seen.

Morphometry. Endometrial thickness in ovariectomized animals was increased significantly by estradiol but not by DHEN. This increase in endometrial thickness was accompanied by an increase in the proportion of the endometrium occupied by glandular tissue, lumen, and stroma (p<0.05) in the ovariectomized estradiol and intact control groups compared with the ovariectomized DHEN-treated group in Table V below.

TABLE V

Endometrial morphometry in female rhesus macaques

| Group | Average thickness (mm) | Greatest thickness (mm) | Glands (%) | Lumen (%) | Epithelium (%) |
|---|---|---|---|---|---|
| Intact control | 1.81 (0.23) | 2.19 (0.29) | 31.4 (4.0) | 7.6 (1.4) | 13.8 (2.9) |
| Ovariectomized control | 0.55 (0.18)* | 0.72 (0.23)* | 12.7 (3.3)* | 3.2 (1.1) | 9.6 (2.3)* |
| Ovariectomized DHEN | 0.69 (0.19)* | 0.89 (0.24)* | 12.9 (3.4)* | 2.6 (1.2)* | 10.3 (2.4)* |
| Ovariectomized plus $E_2$ | 1.31 (0.25) | 1.64 (0.31) | 24.9 (4.5) | 4.3 (1.5) | 20.6 (3.2) |

$E_2$ Estradiol.
*$p < 0.05$, compared with intact control and ovariectomized plus estradiol groups In the mammary gland, total gland thickness was greatest in the intact control animals, which differed significantly from ovariectomized controls and DHEN-treated animals (p<0.05) but not from estradiol-treated animals. Maximal lobular size and percentage of the gland occupied by epithelium were greatest in estradiol-treated animals; however, no groups differed statistically in these mammary morphometric parameters.

Immunohistochemistry. Treatment-related differences in Ki-67 staining in the endometrial epithelium were significant (p=0.0048 for overall differences). Ki-67 staining was maximal in the endometrial epithelium of animals given estradiol (mean, 32% of cells), followed by intact controls (mean, 14% of cells). Estradiol-treated animals differed from ovariectomized controls and DHEN-treated females (p<0.05) but not from intact controls. Intact cycling animals did not differ from any group. DHEN-treated animals (mean 5% of cells) did not differ from controls (mean, 4% of cells) (see Table VI).

TABLE VI

Endometrial proliferation in female rhesus macaques

| Group | Cells staining with Ki-67 (%) |
|---|---|
| Intact control | 14.9 (5.1) |
| Ovariectomized control | 4.2 (4.7)* |
| Ovariectomized DHEN | 5.4 (4.7)* |
| Ovariectomized plus estradiol | 32.3 (6.3) |

Amounts are mean ± SE.
*$p < 0.05$, compared with intact control and ovariectomized plus estradiol groups; ovariectomized plus estradiol and intact control groups were not different.

Based on the aforementioned studies, one week of DHEN treatment prevented acetylcholine-induced endothelium-dependent vasoconstriction in both the males and the ovariectomized females compared with control males and ovariectomized control females, respectively. It was noted that arteries in the ovariectomized estradiol group constricted to both acetylcholine and nitroglycerine. This was puzzling because plasma estradiol concentrations were high enough to have prevented acetylcholine-induced vasoconstriction and vasoconstriction to nitroglycerin [Williams, J K et al, *Circulation, supra*]. These results may have been due to the additional stress induced by the brief anesthesia required for subcutaneous insertion of the Silastic silicone rubber (Dow Corning, Midland, Mich.) rods containing estradiol.

DHEN treatment for 5 weeks at a dose of about 0.3 mg/kg/day had no apparent effect on plasma lipid, lipoprotein, or apolipoprotein concentrations or fasting glucose and insulin concentrations in ovariectomized female macaques. This is quite different from the profound reduction of total plasma cholesterol concentrations we observed at a similar dose in ovariectomized rats. Similarly, in male rhesus macaques treated with fourfold higher doses, DHEN had no effects on plasma total cholesterol, HDL, triglyceride, or apolipoprotein B concentrations, but did have a 31% increase in apolipoprotein A-l (the predominant apolipoprotein in HDL) and tended toward lower apolipoprotein E concentrations. Fasting insulin concentrations were 43% lower in DHEN-treated males with no effect on fasting plasma glucose concentrations. The lack of lipid and lipoprotein effects with DHEN treatment may be due to fundamental differences in rodent and nonhuman primate lipid and lipoprotein physiologic mechanisms. However, the dose of the drug and the very short treatment period also may have contributed to the lack of an effect on plasma lipid and lipoprotein concentrations.

Unlike estradiol, DHEN has no apparent proliferative or trophic effects on the mammary glands, uterus, or endometrium of ovariectomized female macaques. Similarly, in spite of a small decrease in plasma testosterone concentrations, there was no decrease in either prostatic or testicular weight in the males treated with DHEN.

The present studies demonstrated several interesting and potentially important effects of DHEN on the cardiovascular system of both male and ovariectomized female rhesus macaques. Most of the effects were seen in males, and the absence of similar effects in females may be due to the lower dose used in the females compared with the males. However, gender differences in the mechanisms of action of DHEN cannot be excluded.

DHEN preserved endothelium-dependent vasodilation in males and prevented the coronary vasoconstriction associated with ovariectomy in females. Prevention of endothelium-dependent vasoconstriction in males was not observed with short-term administration of estradiol to men, but has been observed in men when given 20 minutes after administration of 1.25 mg Premarin intravenously. [Collins P et al., 17β-Estradiol attenuates acetylcholine-induced coronary arterial constriction in women but not men with coronary heart disease. *Circulation* 1995;92:24–30; and Reis S E et al., Estrogen has an acute beneficial effect on coronary vasoreactivity in man [abstract]. *Circulation* 1995;92:1–249.] Preservation of endothelium-dependent vasodilation in males may be a unique property of DHEN and conjugated equine estrogens.

Additionally, it is unclear whether DHEN may be a more potent vasodilator in females than estradiol because the ovariectomized monkeys treated with subcutaneous estradiol had a slightly different treatment than ovariectomized females treated with oral DHEN. Prevention of endothelium-dependent vasoconstriction may reduce shear forces on plaques, which lead to plaque rupture and arterial thrombosis and consequent myocardial ischemia and infarction.

The increase in apolipoprotein A-1 concentrations in the males may result in an increase in cholesterol transfer from LDL to HDL, thus, decreasing the amount of cholesterol available for plaque formation. The decrease in plasma insulin concentrations that did not affect fasting plasma glucose concentrations implies that insulin sensitivity was increased with DHEN treatment.[see Cefalu W T et al., supra]. The reduction in insulin concentrations may also reduce the atherogenic effects of hyperinsulinemia.

DHEN has been shown to reduce arterial LDL accumulation in males, but had no effect in females [Wagner J D et al, supra]. This dose in females may have been inadequate to achieve this effect. DHEN also reduces arterial peroxidation in ovariectomized females, and there was a trend toward reduction of arterial peroxidation in the males (unpublished data). These data are consistent with previously published data on the antioxidant properties of the ring B unsaturated conjugated equine estrogens [Subbiah M T R et al., Antioxidant potential of specific estrogens on lipid peroxidation. *J Clin Endocrinol Metab* 1993;77: 1095–7; and Wilcox J G et al., The biological effects of individual estrogen components in conjugated equine estrogens (CEE) and their possible modulation of insulin resistance and oxidation of LDL [abstract]. *J Soc Gynecol Invest* 1995;2:153].

It is unclear why the higher dose in the males was less effective in preventing arterial peroxidation than the lower dose used in the ovariectomized females, but this may have been caused by peroxidant effects of circulating testosterone and less efficient concentration of DHEN in tissues resulting from gender differences in estradiol receptor density. Both the reduction of arterial LDL accumulation and arterial peroxidation products may decrease atherogenesis.

In view of the foregoing, DHEN holds promise as an intervention for reducing atherogenesis by (1) preventing endothelium-dependent vasoconstriction in both males and ovariectomized females, (2) increasing apolipoprotein A-1 and decreasing apolipoprotein E concentrations, (3) decreasing plasma insulin concentrations, (4) reducing LDL accumulation, and (5) reducing arterial peroxidation. DHEN may also have important effects on clotting function and prostaglandin, cytokine, and growth factor production and function that are as yet unexplored.

In the present invention, DHEN did not appear to have any proliferative or trophic effects on female macaque reproductive or mammary organs. Therefore it is possible that, if used in hormone replacement therapy regimens, a concomitant progestin for prevention of endometrial carcinoma could be eradicated. DHEN would not be expected to induce mastalgia or mammary proliferation. These properties might lead to increases in acceptance and long-term adherence to hormone replacement therapy regimens by postmenopausal women. Additionally, DHEN does not appear to have any adverse effect on the male genitourinary system. Thus, DHEN may be a useful treatment for men in prevention of ischemic heart disease.

Finally, in these studies, the anti-atherogenic properties of DHEN and its lack of trophic reproductive organ and mammary effects were presumed from promising intermediate markers after an extremely short treatment period. All these end points should be tested in appropriately designed long-term trials.

Dosage Requirements

When DHEN is used in accordance with the present invention, it can be formulated into normal dosage forms such as capsules, tablets, powders, suspensions, emulsions, solutions, syrups, aerosols, soft and hard gelatin capsules, suppositories, injectable solutions and the like. DHEN can be administered by itself or in combination with pharmaceutically acceptable carriers, diluents, stabilizers, solubilizers, lubricants, binders and the like or excipients thereof. Regardless of the pharmaceutical formulation, 17α-dihydroequilenin will be found in a proportion that will impart the desired activity to the mammal.

Oral dosing of DHEN is the preferred form of administration. However, other routes of administration are contemplated. For example, DHEN may be injected parenterally, in which case it is administered in the form of a sterile solution containing other components such as glucose or saline. It is further contemplated that DHEN may be administered transdermally with the use of a transdermal patch containing the active ingredient, DHEN and a pharmaceutical carrier. The transdermal patch allows the delivery of DHEN to the skin for systemic absorption into the blood stream. The dosage requirements for DHEN for administration to patients will be based upon dosage requirements to achieve atherosclerotic benefits without endometrial proliferation in menopausal females or feminizing effects in males.

Based on the aforementioned animal studies, the approximate dosage requirements for humans are expected to approximate those of the metabolic equivalents for rhesus monkeys. It is believed that metabolically equivalent doses in men and women to those tested in macaques will achieve similar beneficial effects without any adverse effects on the uterus, breast, prostate and testes. Of course, precise dosages for any form of administration to the patient will be determined by more comprehensive dose-finding studies and by the administering physician based on his or her experience with the patient being treated.

Generally, 17α-dihydroequilenin should be administered at a concentration that will achieve the desired result without causing any harmful or deleterious side effects. While it is contemplated that 17α-dihydroequilenin has demonstrated potential as a single-agent therapeutic regimen, it is contemplated that this compound may be combined with another hormonal compound to enhance the overall beneficial effects of 17α-dihydroequilenin.

Dose-Finding Studies

Table VII illustrates the composition of Premarin® and the relative potencies of the various component conjugates as a function of cornification of the vaginal epithelium of ovariectomized rats (Allen-Doisy test) [Lyman G W et al., Assay for conjugated estrogens in tables using fused-silica capillary gas chromatography. *J Chromatogr* 1982;234:234–9; and Stern M. Pharmacology of conjugated oestrogens. Maturitas 1982;4:33–9].

TABLE VII

Components of Premarin (all estrogens are sulfate salts)

| Compound | Component (%) | Relative Potency |
| --- | --- | --- |
| Estrone | 49.1 | 0.30 |
| Equilin | 22.8 | 0.42 |
| 17α-Dihydroequilin | 13.5 | 0.0006 |
| Δ-8,9-Dehydroestrone | 3.9 | Not tested |
| 17α-Estradiol | 3.7 | 0.0011 |
| Equilenin | 2.8 | 0.013 |
| DHEN | 1.6 | 0.00018 |
| 17β-Dihydroequilin | 1.5 | 0.83 |
| 17β-Dihydroequilenin | 0.7 | 0.0021 |
| 17β-Estradiol | 0.56 | 1.0 |
| Premarin | Whole preparation | 0.38 |

The preliminary dose-finding study that preceded the larger study detailed in the present invention was a randomized placebo-controlled study with two groups of ovariectomized females (n=5 per group) and four groups of males (n=5 per group). The study was begun after a period of acclimatization to a moderately atherogenic diet containing approximately 0.3 mg cholesterol/cal. Plasma concentrations of total cholesterol, HDL, and triglycerides were determined at 2, 4, and 8 weeks after initiating treatment. Animals were randomized to treatment by lifetime exposure to dietary cholesterol and by baseline total plasma cholesterol/HDL ratio. The dose used in the females was 0.312 mg/kg/day, which was metabolically equivalent to the middle dose in our rat study. [Washburn S A et al., supra.] No other doses in the females were explored because we wanted to determine the effect of DHEN in ovariectomized female rhesus macaques at a metabolically equivalent dose to the one used in the ovariectomized rats. The males did undergo an abbreviated dose-ranging study. The doses for the males were 0.312 mg/kg/day (identical to the female dose), 0.625 mg/kg/day, and 1.25 mg/kg/day.

As illustrated in FIGS. 3 and 4, there were no statistical differences among groups for any dose in either the females or the males compared with the controls. However, it was hoped that the trends in the lipid and lipoprotein concentrations might predict significant effects in other cardiovascular assessments, especially coronary vasomotion and LDL accumulation or degradation.

All references referred to herein are hereby incorporated by reference in their entirety.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method of improving insulin sensitivity in a mammal by reducing insulin concentrations, comprising administering a therapeutically effective amount of 17α-dihydroequilenin or a mammalian metabolic conjugate thereof to a mammal in need of such treatment.

2. The method according to claim 1, wherein the administered compound is 17α-dihydroequilenin sulfate.

3. The method according to claim 1, wherein the route of administration for 17α-dihydroequilenin is selected from the group consisting of oral, intravenous, parental, transdermal, rectal, intravaginal, intranasal, and intrabronchial administration.

4. The method according to claim 1, wherein the mammal is a male or female.

* * * * *